United States Patent [19]
Model

[11] 3,971,805
[45] July 27, 1976

[54] IMINOISOINDOLINONE PIGMENTS AND PROCESS FOR THEIR MANUFACTURE

[75] Inventor: Ernst Model, Basel, Switzerland

[73] Assignee: Ciba-Geigy Corporation, Ardsley, N.Y.

[22] Filed: Apr. 17, 1975

[21] Appl. No.: 569,041

[30] Foreign Application Priority Data
Apr. 30, 1974 Switzerland.................. 5909/74

[52] U.S. Cl............................. 260/325 PH; 8/54.2; 106/23; 106/288 Q; 260/37 P; 260/39 P; 260/42.21
[51] Int. Cl.²...................................... C07D 209/46
[58] Field of Search............................. 260/325 PH

[56] References Cited
UNITED STATES PATENTS
2,973,358   2/1961   Pugin............................ 260/325 PH
3,867,404   2/1975   von der Crone et al. ..... 260/325 PH

*Primary Examiner*—Lewis Gotts
*Assistant Examiner*—S. P. Williams
*Attorney, Agent, or Firm*—Vincent J. Cavalieri

[57] ABSTRACT

Iminoisoindolinone pigments of the formula

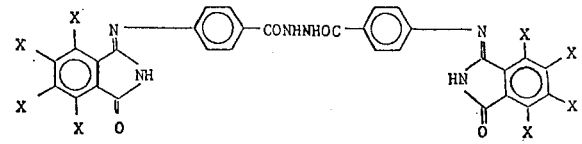

wherein the X denote chlorine or bromine atoms are useful for coloring plastics and lacquers in fast yellow shades.

2 Claims, No Drawings

IMINOISOINDOLINONE PIGMENTS AND PROCESS FOR THEIR MANUFACTURE

It has been found that new valuable iminoisoindolinone pigments of the formula

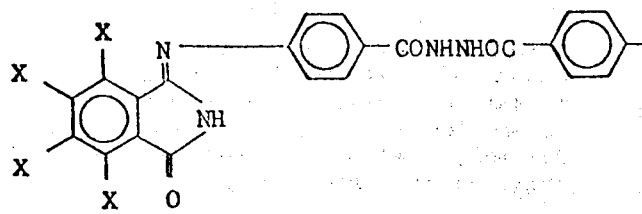 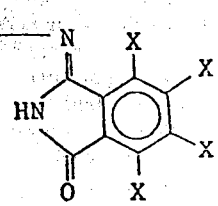

wherein the X denote chlorine or bromine atoms, are obtained when an isoindolinone of the formula

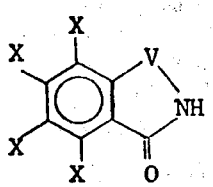

wherein the X have the indicated meaning and V denotes a group of the formula

wherein $X_2$ denotes an imino or thio group and the $Y_2$ represent halogen atoms, alkoxy groups or secondary amino groups, is condensed with the diamine of the formula

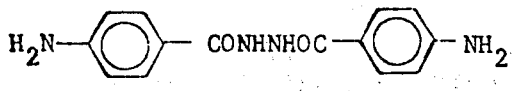

in the molar ratio of 2 : 1.

The pigment of the indicated formula, wherein the X denote chlorine atoms, is of particular interest.

The starting materials used are preferably isoindolinones of the formula

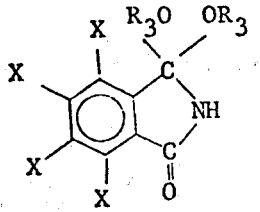

wherein X has the indicated meaning and $R_3$ denotes an alkyl group containing 1–4 carbon atoms, and especially those wherein the X denote chlorine atoms.

The following may be mentioned as examples of isoindolinones: 3,3-dimethoxy-4,5,6,7-tetrachloroisoindolinone and 3,3-dimethoxy-4,5,6,7-tetrabromoisoindolinone.

The isoindolinones mentioned are known compounds.

The condensation of the isoindolinone with the amine is in some cases carried out in the cold, and where appropriate with warming of the intimately mixed components, particularly advantageously in the presence of organic solvents which are inert, that is to say which do not participate in the reaction.

If the starting materials are 3-imino-, 3-thio- or 3,3-bis-sec.amino-4,5,6,7-tetrachloroisoindolin-1-ones or alkali metal salts of 3,3-dialkoxy-4,5,6,7-tetrahalogenoisoindolin-1-ones, it is advantageous to use water-miscible organic solvents, for example lower aliphatic alcohols, such as lower alkanols, for example methanol, isopropanol or butanol, lower cyclic ethers, such as dioxane, ethylene glycol monomethyl ether or lower aliphatic ketones, such as acetone. The condensation in these cases takes place even at relatively low temperatures. It is advantageously carried out in the presence of agents which bind bases; as examples of such agents, lower fatty acids, which then simultaneously serve as solvents, and especially acetic acid, should be mentioned.

If 3,3,4,5,6,7-hexahalogenoisoindolin-1-ones are used, it is preferred to employ organic solvents which are free from hydroxyl groups, such as hydrocarbons, for example aromatic hydrocarbons, such as benzene, toluene, xylene, tetrahydronaphthalene or diphenyl, or cycloaliphatic hydrocarbons, for example cyclohexane, or halogenohydrocarbons, such as aliphatic halogenohydrocarbons, for example carbon tetrachloride or tetrachloroethylene, or aromatic halogenohydrocarbons, such as chlorobenzene or dichlorobenzenes and trichlorobenzenes, as well as aromatic nitrohydrocarbons, such as nitrobenzenes, ethers, including aliphatic ethers, such as dibutyl ether, aromatic ethers, such as diphenyl ether, or cyclic ethers, such as dioxane, and also ketones, such as acetone, or esters, especially esters of lower fatty acids with lower alkanols, such as ethyl acetate, in the presence of acid-binding agents.

The new pigments precipitate from the reaction medium immediately after they have formed. For certain purposes they can be used directly as crude pigments; however, it is also possible to improve their properties further, especially with regard to purity, form and hiding power, in accordance with methods which are in themselves known, for example by extraction with organic solvents or by grinding with grinding auxiliaries which can subsequently be removed again, for example salts, or by alkaline reprecipitation.

The new colorants are valuable pigments which can be used, in a finely divided form, for pigmenting high molecular organic material, for example cellulose ethers and cellulose esters, such as ethylcellulose, acetylcellulose and nitrocellulose, polyamides, polyurethanes or polyesters, natural resins or synthetic resins, for example aminoplasts, especially urea-formaldehyde and melamine-formaldehyde resins, alkyd resins, phenoplasts, polycarbonates, polyolefines, such as polystyrene, polyvinyl chloride, polyethylene, polypropylene, polyacrylonitrile, polyacrylic acid esters, thermoplastic or curable acrylic resins, rubber, casein, silicone and silicone resins, individually or as mixtures. It is immaterial whether the high molecular compounds mentioned are in the form of plastic masses, melts or spinning solutions, lacquers or printing inks. Depending on the end use, it proves advantageous to employ the new pigments as toners or in the form of preparations.

The colorations obtained are distinguished by great depth of colour, a greenish-tinged yellow colour shade of high purity, depth of colour and transparency, good fastness to over-lacquering, light and weathering and stability to plastics additives. Compared to the isoindolinone pigments from 2,5-bis-(4′-aminophenyl)-oxydiazole (obtainable by cyclisation of the bis-(4′-aminobenzoyl)-hydrazide, to be used according to the invention, with elimination of water) described in German Pat. No. 1,098,126, the pigments according to the invention are distinguished by greater depth of colour and brilliance and better fastness properties.

EXAMPLE 1

16.5 g of 3,4,5,6-tetrachloro-2-cyanobenzoic acid methyl ester are stirred with 55 ml of a 1 N sodium methylate solution in methanol to give a clear solution. The sodium salt of 3,3-dimethoxy-4,5,6,7-tetrachloroisoindolin-1-one is produced. 6.75 g of 4,4′-diamino-N,N′-dibenzoyl hydrazide are now flushed in with a little methanol. The reaction mixture is now stirred for 1 hour at a bath temperature of 70° (internal temperature 55°–60°) and after dilution with 100 ml of o-dichlorobenzene is brought to an internal temperature of 100° whilst distilling off methanol. After addition of a further 100 ml of o-dichlorobenzene and 20 ml of glacial acetic acid, the temperature is raised to 140°–150° and maintained for 2 hours. The insoluble colorant is filtered off at 120° and washed with methanol, acetone and water. After drying in vacuo at 90°, 18 g of a yellow pigment are obtained which can be used directly, in this form, for incorporation into lacquers, into high molecular compositions and into printing inks.

EXAMPLE 2

If, in the preceding example, the 3,4,5,6-tetrachloro-2-cyanobenzoic acid methyl ester is replaced by a corresponding amount of 3,4,5,6-tetrabromo-2-cyanobenzoic acid methyl ester, a yellow pigment with comparably good properties is obtained.

EXAMPLE 3

2 g of the pigment prepared according to Example 1 are mixed, and ground, with 36 g of hydrated alumina, 60 g of linseed oil varnish of medium viscosity and 0.2 g of cobalt linoleate on a triple-roll mill. The yellow prints produced with this colorant paste are distinguished by excellent fastness to light.

EXAMPLE 4

0.6 g of the pigment prepared according to Example 1 is mixed with 67 g of polyvinyl chloride, 33 g of dioctyl phthalate, 2 g of dibutyl-tin dilaurate and 2 g of titanium oxide and the mixture is milled on a triple-roll mill for 15 minutes. The yellow polyvinyl chloride films produced with the mixture have a colour which is fast to migration, heat and light.

EXAMPLE 5

10 g of titanium oxide and 2 g of the pigment prepared according to Example 1 are ground for 48 hours in a ball mill with 88 g of a mixture of 26.4 g of coconut alkyd resin, 24.0 g of melamine-formaldehyde resin (50% solids content), 8.8 g of ethylene glycol monomethyl ether and 28.8 g of xylene.

If this lacquer is sprayed onto an aluminium foil, pre-dried for 30 minutes at room temperature and then stoved for 30 minutes at 120°C, a greenish-tinged yellow lacquering is obtained, which is distinguished by very good fastness to over-lacquering, light and weathering.

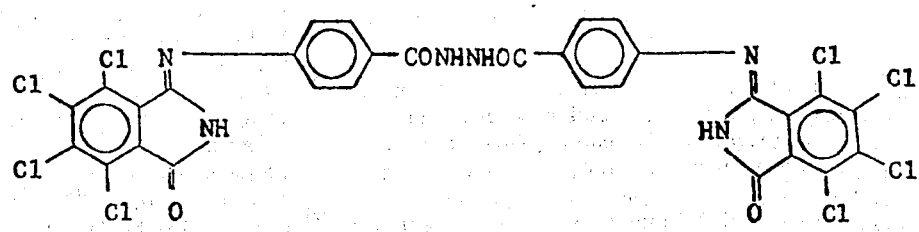

I claim:

1. An iminoisoindolinone pigment of the formula

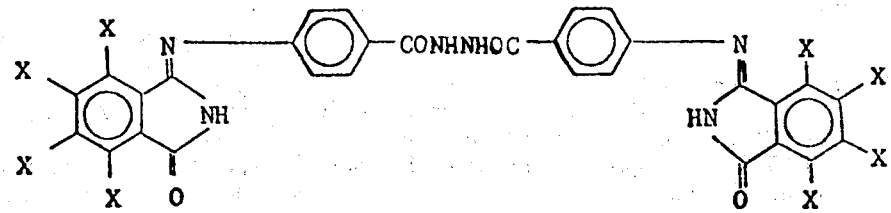

wherein the X denote chlorine or bromine atoms.

2. The compound as claimed in claim 1 of the formula